United States Patent [19]

Dabroski

[11] 4,202,925
[45] May 13, 1980

[54] PAPER SURGICAL TAPE

[75] Inventor: Winifred C. Dabroski, East Brunswick, N.J.

[73] Assignee: Johnson & Johnson, New Brunswick, N.J.

[21] Appl. No.: 893,373

[22] Filed: Apr. 4, 1978

[51] Int. Cl.² ............................ B32B 7/00; C09J 7/02
[52] U.S. Cl. .................................... 428/219; 428/261; 428/262; 428/264; 428/265; 428/341; 428/342; 428/354; 428/352; 428/422; 428/447; 428/514; 128/156; 427/382; 427/391; 162/168 R; 162/146
[58] Field of Search ............... 428/219, 261, 262, 264, 428/265, 341, 342, 354, 352, 422, 447, 514; 128/156

[56] References Cited

U.S. PATENT DOCUMENTS

| | | | |
|---|---|---|---|
| 3,121,021 | 2/1964 | Copeland | 428/219 |
| 3,154,430 | 10/1964 | Goodloe et al. | 427/382 |
| 3,523,846 | 8/1970 | Muller | 156/78 |
| 3,677,788 | 7/1972 | Zirnite | 428/352 X |

*Primary Examiner*—P. C. Ives

[57] ABSTRACT

An adhesive tape which includes an acrylic pressure sensitive adhesive mass coated on one side of a saturated paper, said paper (1) being saturated with from 20 to 75 parts per hundred parts paper of an acrylic polymer having a $T_g$ of less than 20° C., and (2) comprising a mixture of woodpulp and thermoplastic fibers, said woodpulp comprising from about 10 to 75% by weight of the paper, and said thermoplastic fibers ranging in length, on the average, from about $\frac{1}{4}$ to $\frac{3}{4}$ of an inch and being selected from the group consisting of polyamide, polyester, polypropylene and polyethylene fibers, and a backsize coated on the other side of said paper, said backsize preferably being selected from the group consisting of styrene copolymers having a $T_g$ of at least 35° C., silicones, fluorocarbons, long chain fatty acids, long chain fatty acid derivatives and mixtures thereof. Preferably the pressure sensitive mass is a blend of a copolymer of 2 ethylhexyl acrylate and vinyl acetate with a copolymer of 2 ethylhexyl acrylate and tert-butyl acrylamide.

The instant tape is especially useful as a surgical tape and has an improved combination of the properties of conformability, straight tear and resistance to curling. Moreover, because of the high amounts of woodpulp included in the paper utilized in making the instant tape, an economical product is obtained.

10 Claims, No Drawings

PAPER SURGICAL TAPE

FIELD OF THE INVENTION

The instant invention relates to novel adhesive tapes in which the paper utilized in making the tape includes wood pulp in combination with thermoplastic fibers selected from the group consisting of polyamides, polyesters and polyolefins, having an average length of from about 1/4" to about 3/4". The tapes of this invention include a pressure sensitive acrylic adhesive mass, preferably a blend of a copolymer of 2-ethylhexyl acrylate and vinyl acetate with a copolymer of 2 a ethylhexyl acrylate and N-tert-butyl acrylamide and a backsize such as a styrene copolymer having a $T_g$ of greater than 35° C. coated on the opposite side.

BACKGROUND OF THE PRIOR ART

Pressure sensitive adhesive tapes, which include a pressure sensitive adhesive coated on a paper substrate and are used as surgical tapes are well known in the art. It is appreciated that the inclusion of thermoplastic fibers having an average length of at least 1" in the paper substrate will improve certain qualities such as resistance to curling of the adhesive tape. However, adhesive tapes based on such paper substrates are difficult to tear in a straight line. See, for example, the tape disclosed in U.S. Pat. No. 3,121,021.

Surgical adhesive tapes which utilize a paper substrate including wood pulp in combination with rayon fibers of an average length less than 1/4" are also known. These tapes tear in a very straight manner, but have a tendency to curl when removed from a roll. See for example, the adhesive tape disclosed and claimed in U.S. Pat. No. 3,677,788. This curling has led to problems of adhesion when tapes of the kind disclosed in said patent are applied to a surface such as a human body. In particular, the adhesive tape has a tendency to lift at the ends. It was believed by those skilled in the art, that this problem could be solved by increasing the weight of the pressure sensitive adhesive mass on the tape, or by using a more aggressive mass, however, these solutions still did not completely alleviate the problem of edge lifting and an agressive mass increased skin maceration.

SUMMARY OF THE INVENTION

It has now been unexpectedly found and is the subject of this invention, that a novel paper tape, which does not suffer from the above problem of end lifting and which maintains the desirable properties, such as straight edge tear, of the tape disclosed in the U.S. Pat. No. 3,677,788, can be prepared as further shown below. Moreover, this novel paper tape has improved porosity when compared to the prior art tape disclosed in the '788 patent and does not require the step of micropleating the tape backing. Micropleating as known in the art, causes a loss in tensile strength, and moreover adds to the cost since both an extra step is needed in the manufacturing process and the equipment on which the micropleating operation is carried out is expensive.

The properties of the novel paper tape of this invention are achieved by use of a specially formulated and treated paper which has a pressure sensitive porous adhesive coat on one surface and preferably a release coating on the opposite surface. The special formulation of the paper includes a short fiber, randomly dispersed blend of wood pulp and thermoplastic fibers which are selected from the group consisting of polyester, polyamide and polyolefins, saturated with a flexible polymer.

The wood pulp keeps the cost low and the thermoplastic fibers contribute to softness, flexibility, delamination resistance and improved conformability to a degree that is sufficient to alleviate the end lifting problem of the prior art tapes. The shortness of the fibers provide straight edge tear characteristics to the tape. Further details of the invention are given below.

The Paper

The aforesaid paper, which may have a thickness of 2 to 21 mils, or otherwise as desired, comprises a blend of 10 to 75% by weight wood pulp and correspondingly 90 to 25% by weight of the thermoplastic fiber, all of said fibers having a length not substantially in excess of about 3/4 of an inch, i.e. an average length of from 1/4 to 3/4 inches, preferably an average of from about 1/4 to about 1/2 inch, and most preferably an average of about 3/8 inch. The fibers are uniformly randomly dispersed throughout the paper and are bound together by a flexible binder such as a soft (having a $T_g$ of $<20°$ C.) crosslinkable rubbery binder, e.g. an acrylate binder. The binder is present in the amount of about 20 to 75, typically about 30 to 50 pph. All proportions of the constituents of the tape set forth above and hereinafter are given in weight percent based upon the paper or parts per hundred parts paper (pph).

In a specific embodiment the paper may have a thickness of about 3-6 mils and comprises a random blend of 10 to 75% by weight wood pulp and correspondingly 90 to 25% by weight of a polyester fiber of an average of about 3/8 inch length and about 40 pph of a crosslinked polyethyl acrylate as the binder.

The paper may be prepared by techniques known in the art of paper making. However, it is preferred that the resin binder be incorporated in a post saturation step, that is, the paper is made without any binder. The binder is then applied by immersing the sheet in a latex bath, and squeezing out the excess to get the desired level of resin impregnation. It is believed that post saturation of the paper improves the delamination resistance of the finished tape.

The Pressure-Sensitive Adhesive

The adhesive which is applied to the above paper can be any conventional, preferably porous, pressure-sensitive adhesive used in the preparation of surgical tapes, adhesive bandages and the like, the particular type per se not being part of the present invention other than being a necessary part of the claimed construction. Suitable adhesives are, for example, the acrylate pressure-sensitive adhesives presently used in surgical adhesive tape construction. Rubber-base adhesives such as those made from natural or synthetic rubber are not preferred due to their lack of hypoallergenic properties.

One operable form of pressure-sensitive adhesive is a pure rubbery copolymer of isooctyl acrylate and acrylic acid in 94:6 ratio, as described in U.S. Pat. No. 2,884,126 (re. 24,906). A technique for developing the desired and necessary microporous structure therein so as to achieve a high moisture vapor transmission rate (MVTR) e.g., about 50 to 500 grams per 100 square inches in 24 hours, is described in U.S. Pat. No. 3,121,021.

Preferred formula adhesives are 2-ethylhexyl acrylate-vinyl acetate copolymer or a blend of this copolymer with 2-ethylhexyl acrylate-n-tert-butyl acrylamide copolymer, the mixture cross-linked, or cured, with a suitable catalyst, e.g., Zirco dryer, a zirconium organic complex catalyst sold by Advance Solvents & Chemical. Other operable adhesives are described, for example, in U.S. Pat. Nos. 2,877,141; 2,909,278; 3,307,544 and 3,325,459.

The adhesive may be applied to the paper by conventional techniques, including, for example, transfer techniques, spray techniques, the use of a "kiss" roll, or reverse roll coating and the like. The adhesive mass is generally firmly bonded to the paper, no primer normally being required to anchor the mass. Volatiles may be flashed from the mass as soon as applied so that solids will not penetrate too deeply into or bleed through the paper.

In a typical transfer technique, the adhesive mass may be cast from a solvent on a release paper having a heat-resistant, insoluble anti-stick surface, e.g. a silicone release coated carrier. It is passed through an oven to remove the solvent and, if necessary, to blow and cure the mass. The paper of the present invention is then laminated to the mass by being pressed down thereon at the end of the oven line, the release paper ultimately being stripped away.

When applying the mass by spraying, the volatiles therein are flashed and the mass is disposed on the paper in a stringy pattern. The stringy mass is anchored during the subsequent oven treatment, resulting in a highly breathable coating.

The amount of adhesive depends upon the particular adhesive, the end use of the product, and the like. In a typical surgical tape embodiment, the weight of the dry adhesive layer may be in the range of about 0.4 to 1.6 ounces per square yard. Due to the unique properties of the paper used in making the tape products of this invention, the weight of adhesive mass can be decreased while maintaining good tape properties. For example, it has been found that the paper tape of the instant invention having an adhesive mass of 0.8 ounces per square yard is equivalent to the adhesive tape of U.S. Pat. No. 3,677,788 at an adhesive mass level of 1.2 ounces per square yard. A typical porosity (MVTR) for the paper after application of the above-described preferred adhesive may be in the range of 50 to 100 grams per 100 square inches per 24 hours.

Release Coating

A release coating is usually considered necessary because wood-pulp containing blends have relatively low delamination or splitting resistance. However, the instant novel tape as noted above may be prepared by a post saturation technique which improves the delamination resistance. Even still it is preferred to incorporate a release coating in order to have a low peel force or unwind tension when unwinding the resultant tape from a roll thereof. Therefore, a backsize is applied on the adhesive-free surface before, after or simultaneously with the pressure-sensitive adhesive, preferably before.

Suitable backsizes are described in the U.S. Pat. No. 2,913,355 and others will be apparent to those skilled in the art and may be checked for suitability by simple experimentation. Specific examples of backsizes include stearyl methacrylate acrylonitrile, suitably cured and silicone-based backsizes, e.g., Silicolease 425 (rapid-curing release coating sold by Imperial Chemical Industries America, Inc.). Water-based backsizes are preferred due to the greater ability to maintain a nonpenetrable viscosity.

Conventional application techniques may be employed. For example, the backsize is preferably applied by gravure roll techniques. When the backsize has a low solids content, e.g., less than about 20%, the backsize may also be sprayed on the surface of the paper web whereby much of the solvent evaporates during the spraying, the solids concentration is increased, and little of the solids content penetrates into the paper. As a result, the surface of the paper is coated with discrete particles of the backsizing agent anchored to the paper surface.

In one preferred embodiment two different backsizes are applied sequentially to the adhesive tape. For example, a styrene copolymer having a $T_g$ of greater than 35° C., e.g., a styrene-ethylacrylate-butadiene copolymer is applied from a latex. After drying to remove excess water a silicone release agent is applied on top of the styrene copolymer. The styrene copolymer may be applied at a level of from 0.1 to 0.3 and the silicone may be applied at a level of from 0.01 to 0.1 ounces per square yard of tape.

Preferably the paper tape is prepared by coating the above described post saturated paper with the backsize, followed by drying and then direct coating the adhesive on the opposite side of the paper.

In general, however, the instant paper tape may be prepared by the methods disclosed in U.S. Pat. No. 3,677,788 which is hereby incorporated by reference.

The following are specific examples of the instant invention. There is no intent, however, to be bound to the scope of these examples.

EXAMPLE I

Comparison of Instant Novel Tape With the Tape of U.S. Pat. No. 3,677,788

Three samples were prepared for this experiment, Sample L and Sample M were examples of the instant novel tape, Sample L was a 3 mil paper of 60/40 woodpulp/polyester ratio saturated with 40 pph of an ethyl acrylate polymer and Sample M was a 6 mil paper of 65/35 polyester/woodpulp ratio saturated with 50 pph of an ethyl acrylate polymer. The average polyester fiber length in both samples was ⅜ of an inch. Sample X was representative of the tape of the '788 patent. The adhesive mass for each of these tapes was the above preferred blend, however, Samples L and M included 0.8 ounces/yard$^2$ adhesive and Sample X included 1.2 ounces/yard$^2$ adhesive. The samples were used to carry out the following tests:

Adhesion to Glass and Backing

The initial and one month aged adhesion values of L and M have adhesion to glass values greater than 40 ounces per inch width and adhesion to backing of 21 oz/in.w. as measured by stripping one inch by eight inch strips at 12 inches per minute and measuring the resisting force on an Instron Tester.

There is a trend in adhesion value drop-off after aging at elevated temperatures. After one month at 120° F. the adhesion to glass values averaged 34 oz/in.w.

Table I

Initial Adhesion Test

| Sample | Adhesion to Glass | Backing |
| --- | --- | --- |

Table I-continued

| | | |
|---|---|---|
| L* | 26 oz/in.w. | 16 oz/in.w. |
| M | 46 oz/in.w. | 28 oz/in.w. |
| X | 26 oz/in.w. | 14 oz/in.w. |

*Sample "L" exhibited mass transfer to glass and tearing along edge.

One Month Aged Samples

| | | Adhesion and Tack | |
|---|---|---|---|
| Sample | Aging Temp. °F. | Adhesion to Glass oz/in.w. | Adhesion to Backing oz/in.w. |
| L | 70 | 55 | 21 |
| L | 100 | 42 | 20 |
| L | 120 | 34 | 20 |
| M | 70 | 42 | 17 |
| M | 100 | 39 | 18 |
| M | 120 | 33 | 20 |
| | | Tack | |

The tack was measured by rolling a steel ball down an inclined plane onto a level surface on which the adhesive tape is supported with the adhesive side up. The distance between the resting place of the steel ball and the juncture of the inclined plane and the level surface is measured and a lower value indicates better tack.

The tack values of all the tapes are excellent before and after one month aging for all samples tested. The values ranged from 1 to 3 cm. Thus, it is clear that the instant novel tapes are equivalent to the commercially acceptable tape of U.S. Pat. No. 3,677,788.

Wear Test, Initial Samples

This test consists of placing eight one inch by three inch strips of tape on twenty-four subjects in a regular rotation which starts with the right arm. The measurement of the adhesion of tape to skin is rated from 0 to 7 in increments of 1 on the basis of area of tape still in contact with the subject.

| Rating | % Stick | Comments |
|---|---|---|
| 0 | 0 | Tape off |
| 1 | 14.3 | Tape almost off |
| 2 | 28.6 | Tape almost off |
| 3 | 42.8 | ½ of tape off |
| 4 | 57.2 | 1 flap almost entirely off |
| 5 | 71.5 | 1 flap up or 4 corners up |
| 6 | 85.6 | 2 corners up slightly or 1 corner up |
| 7 | 100 | All corners adhering firmly |

Both L and M paper tapes were excellent and equivalent to each other and better than Sample X.

A sample of tape which represents the tape disclosed in U.S. Pat. No. 3,121,021 was also tested. See Example Y below. As can be seen from the data given below, this tape had significantly lower adhesion value. Table II gives the weighted average of adhesion after twenty-four and forty-eight hours wear.

Table II

| Sample | 24 Hours | 48 Hours |
|---|---|---|
| L | 92.3 | 82.0 |
| M | 93.5 | 79.9 |
| X | 84.0 | 73.7 |
| X* | 82.8 | 72.0 |

Table II-continued

| Sample | 24 Hours | 48 Hours |
|---|---|---|
| Y** | 67.1 | 56.6 |

*This sample differs from X only in that the adhesive mass is based on a diacetone acrylamide copolymer rather than the above preferred blend.
**Micropore Tape available from 3M Corp.

Samples L, M and X were evaluated for other properties important in a surgical tape. Tensile and Elongation were measured by means of the Instron Tester with 1"×5½" samples and a jaw speed of 12"/minute. Moisture Vapor Transmission Rate (MVTR) was measured by determining the weight % pickup of anhydrous calcium chloride placed in an aluminum dish having an opening with an area of four square inches which is sealed by the experimental tape and placed in an oven at 100° F. and 95% relative humidity for twenty-four hours.

As can be seen from Table III below the instant novel tape has improved tensile and elongation properties although at the higher pressure sensitive adhesive addon the MVTR is low.

Table III

| Sample | Tensile Lbs./in. | Elongation % | MVTR g/100 in²/24 hrs. |
|---|---|---|---|
| L | 10.4 | 17.0 | 146.1 |
| M | 15.6 | 26.1 | 75.5 |
| X | 5.1 | 19.1 | 197.4 |

What is claimed is:

1. A surgical adhesive tape which includes a pressure sensitive adhesive mass coated on one side of a saturated paper, said paper (1) being saturated with from 20 to 75 parts per hundred parts paper of an acrylic polymer having a $T_g$ of less than 20° C., and (2) comprising a mixture of randomly dispersed woodpulp and thermoplastic fibers, said woodpulp comprising from about 10 to 75% by weight of the paper, and said woodpulp and thermoplastic fibers ranging in length, on the average, from about ¼ to ¾ of an inch and said thermoplastic fibers being selected from the group consisting of polyamide, polyester, polypropylene and polyethylene fibers and a backsize coated on the other side of said paper.

2. The tape of claim 1 wherein said backsize is selected from the group consisting of styrene copolymers having a $T_g$ of at least 35° C., silicones, fluorocarbons, long chain fatty acids, long chain fatty acid derivatives and mixtures thereof.

3. The tape of claim 1 wherein said pressure sensitive adhesive is a copolymer of 2-ethylhexyl acrylate and vinyl acetate.

4. The tape of claim 1 wherein said thermoplastic fiber is a polyester.

5. The tape of claim 1 wherein said backsize includes a styrene copolymer.

6. The tape of claim 5 wherein said styrene copolymer is a copolymer of styrene, ethylacrylate and butadiene.

7. The tape of claim 6 wherein said backsize additionally includes a silicone release agent coated on said styrene copolymer.

8. The tape of claim 1 wherein said pressure sensitive adhesive is coated onto said paper at a level of from about 0.6 to about 0.9 ounces per square yard.

9. The tape of claim 1 wherein said backsize is coated on said paper at a level of from about 0.1 to 0.2 ounces per square yard.

10. The tape of claim 3 wherein said pressure sensitive adhesive additionally includes a copolymer of 2-ethylhexyl acrylate and N-tert-butyl acrylamide.

* * * * *